United States Patent [19]

Hayashi et al.

[11] 4,294,849

[45] Oct. 13, 1981

[54] PROSTAGLANDIN ANALOGUES

[75] Inventors: Masaki Hayashi, Takatsuki; Sadahiko Iguchi, Otsu; Takanori Okada, Ibaraki; Akiyoshi Kawasaki, Osaka, all of Japan

[73] Assignee: Warner-Lambert Company, Morris Plains, N.J.

[21] Appl. No.: 114,804

[22] Filed: Jan. 24, 1980

[30] Foreign Application Priority Data

Jan. 29, 1979 [JP] Japan .................................. 54-8904

[51] Int. Cl.³ .................. C07C 177/00; A61K 31/557
[52] U.S. Cl. .................... 424/305; 536/103; 560/121; 562/503; 424/317; 542/426
[58] Field of Search ....................... 560/121; 562/503; 424/305, 317; 536/103; 542/426

[56] References Cited

U.S. PATENT DOCUMENTS 3,931,296  1/1976  Hayashi .............................. 562/503

Primary Examiner—Robert Gerstl

Attorney, Agent, or Firm—Stephen I. Miller

[57] ABSTRACT

Prostaglandin analogues of the formula:-

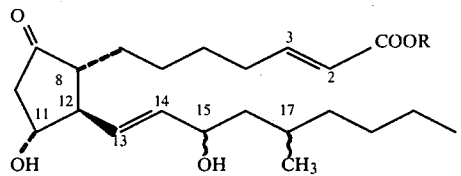

(wherein R represents a hydrogen atom or a straight- or branched-chain alkyl group containing from 1 to 4 carbon atoms, the wavy line indicates attachment in α- or β-configuration or a mixture thereof, and the double bonds between $C_2$-$C_3$ and $C_{13}$-$C_{14}$ are trans), and cyclodextrin clathrates of such acids and esters, and when R represents a hydrogen atom, non-toxic salts of such acids, possess hypotensive activity, inhibitory activity on blood platelet aggregation and vasodilator activity, and weak diarrhoea-producing activity.

11 Claims, No Drawings

PROSTAGLANDIN ANALOGUES

DESCRIPTION

This invention relates to novel prostaglandin analogues to a process for their preparation and to compositions containing them.

In our British Pat. No. 1416410 we have described and claimed inter alia trans-$\Delta^2$-prostaglandin analogues of the general formula:

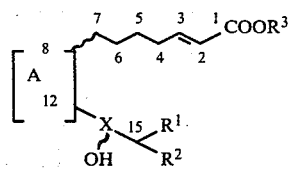

[wherein A represents a grouping of the formula:

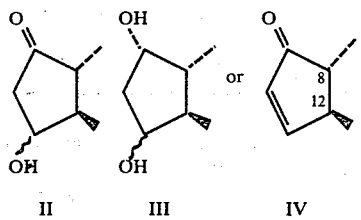

X represents ethylene (i.e. —CH$_2$CH$_2$—) or trans-vinylene (i.e.

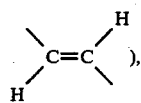), $R^1$ represents a straight-or branched-chain alkyl radical containing from 1 to 10 carbon atoms, or a straight- or branched-chain alkyl radical containing from 1 to 6 carbon atoms carrying a phenyl substituent or a cycloalkyl substituent of 5 to 7 carbon atoms, $R^2$ represents a hydrogen atom or a straight- or branched-chain alkyl radical containing from 1 to 4 carbon atoms, $R^3$ represents a hydrogen atom or a straight- or branched-chain alkyl radical containing from 1 to 10 carbon atoms, the wavy line ⌇ indicates attachment of the hydroxy radical in α- of β-configuration (i.e. S- or R-configuration) or a mixture thereof and the double bond between $C_2$-$C_3$ is in trans-configuration], cyclodextrin clathrates of such acids or esters and, when $R^3$ represents a hydrogen atom, non-toxic salts of such acids, with the exclusion of trans-2,3-didehydro-PGE$_1$. In the aforesaid specification it is disclosed that the compounds possess the known valuable pharmacological properties typical of prostaglandins in a selective fashion including, in particular, hypotensive activity, inhibitory activity on blood platelet aggregation inhibitory activity on gastric acid secretion, and gastric ulceration, and bronchodilator activity and are useful in the treatment of hypertension, in the treatment of disorders of the peripheral circulation, in the prevention and treatment of cerebral thrombosis and myocardial infarction, in the treatment of gastric ulceration and in the treatment of asthma.

However, a known side-effect of prostaglandins is their diarrhoea-producing activity. This side-effect presents difficulties especially when it is desired to administer the compounds orally in the treatment of disorders of the cardiovascular system. Very many prostaglandin analogues have been synthesised with a view to finding new compounds in which there is a wide separation between the dose required to produce a desired therapeutic effect and the dose required to produce the side-effect of diarrhoea. At present no prostaglandin analogues have been found which can be administered orally to treat disorders of the cardiovascular system without producing also the side-effect of diarrhoea.

As a result of research and experimentation directed to the discovery of prostaglandin analogues having stronger hypotensive activity, inhibitory activity on blood platelet aggregation and vasodilator activity and a weaker diarrhoea-producing activity than prostaglandin analogues heretofore known, it has been discovered that trans-$\Delta^2$-prostaglandin analogues of general formula I wherein A represents a grouping of the formula:

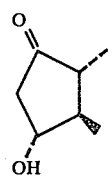

X represents trans-vinylene, $R^1$ represents a 2-methylhexyl group, $R^2$ represents a hydrogen atom, and $R^3$ represents a hydrogen atom or a straight- or branched-chain alkyl group containing from 1 to 4 carbon atoms (i.e. 17,20-dimethyl-trans-2,3-didehydro-PGE$_1$ and certain alkyl esters thereof), cyclodextran clathrates of such acids or esters and, when $R^3$ represents a hydrogen atom, non-toxic salts of such acids have unexpectedly remarkable pharmacological properties.

The present invention relates to prostaglandin analogues of the general formula:

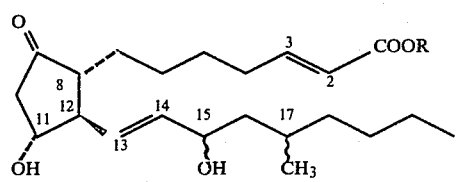

[wherein R represents a hydrogen atom or a straight- or branched-chain alkyl group containing from 1 to 4 carbon atoms, the wavy line ⌇ indicates attachment in α- or β-configuration (i.e. S- or R-configuration) or a mixture thereof, and the double bonds between $C_2$-$C_3$ and $C_{13}$-$C_{14}$ are trans] and cyclodextrin clathrates of such acids and esters, and, when R represents a hydrogen atom, non-toxic )e.g. sodium) salts of such acids.

The present invention is concerned with all such compounds in the 'natural' form as depicted in general formula VI.

As will be apparent to those skilled in the art, the compounds depicted in general formula VI have five centres of chirality, at the carbon atoms in the 8-, 11- and 12-positions of the alicyclic ring and at the 15- and 17- positions in the side chain. The presence of chirality leads, as is well known, to the existence of isomerism. All isomers of general formula VI and mixtures thereof are to be considered within the scope of general formula VI.

The prostaglandin analogues of general formula VI and, when R represents a hydrogen atom, non-toxic salts of such acids have been found to possess extremely strong hypotensive activity, inhibitory activity on blood platelet aggregation and vasodilator activity. They are therefore useful as vasodilators and antihypertensive agents, and are useful for the treatment of cardiac angina and for the prevention and treatment of myocardial infarction, thrombosis and arteriosclerosis. In addition to the above-mentioned valuable pharmacological properties the compounds of the invention possess a very weak diarrhoea-producing activity. This surprising combination of properties in the compounds of the present invention is particularly advantageous in that they can be administered orally for the aforesaid purposes.

For example, in saturated laboratory tests, (i) by intravenous administration to allobarbitalanaesthetised dogs, 9-oxo-11α,15α-dihydroxy-17S,20-dimethylprosta-trans-2,trans-13-dienoic acid, methyl 9-oxo-11α,15α-dihydroxy-17S,20-dimethylprosta-trans-2,trans-13-dienoate and 9-oxo-11α,15α-dihydroxy-17R,20-dimethylprosta-trans-2,trans-13-dienoic acid are 10, 5 and 3.5 times, respectively, a potent as prostaglandin $E_1$ (hereinafter abbreviated to $PGE_1$) in hypotensive activity, (ii) by oral administration to conscious spontaneously hypertensive rats, 9-oxo-11α,15α-dihydroxy-17S,20-dimethylprosta-trans-2,trans-13-dienoic acid and methyl 9-oxo-11α,15α-dihydroxy-17S,20-dimethylprosta-trans-2,trans-13-dienoate are both 100 times as potent as $PGE_1$ in hypotensive activity, (iii) in inhibitory activity on adenosine diphosphate-induced blood platelet aggregation in platelet-rich plasma of humans and rats, 9-oxo-11α,15α-dihydroxy-17S,20-dimethylprosta-trans-2,trans-13-dienoic acid is 81.6 times (in rat plasma) and 38.5 times (in human plasma) as potent as $PGE_1$, and 9-oxo-11α,15α-dihydroxy-17R,20-dimethylprosta-trans-2,trans-13-dienoic acid is 70.5 times (in rat plasma) and 48.1 times (in human plasma) as potent as $PGE_1$, (iv) in coronary vasodilator activity on isolated rabbit hearts, 9-oxo-11α,15α-dihyroxy-17S,20-dimethylprosta-trans-2,trans-13-dienoic acid and 9-oxo-11α,15α-dihydroxy-17R,20-dimethylprosta-trans-2,trans-13-dienoic acid are 19.0 and 14.0 times, respectively, as potent as $PGE_1$, and (v) by oral administration to mice, 9-oxo-11α,15α-dihydroxy-17S,20-dimethylprosta-trans-2,trans-13-dienoic acid, methyl 9-oxo-11α,15α-dihydroxy-17S,20-dimethylprosta-trans-2,trans-13-dienoate and 9-oxo-11α,15α-dihydroxy-17R,20-dimethylprosta-trans-2,trans-13-dienoic acid show a lower diarrhoea-inducing activity than $PGE_1$.

In the use of the compounds of the present invention as vasodilators or antihypertensive agents, or for the treatment of cardiac angina, or for the prevention and treatment of myocardial infarction, thrombosis and arteriosclerosis, hypotensive activity, inhibitory activity on blood platelet aggregation and vasodilator activity in the above-described pharmacological properties are useful activities, whereas diarrhoea-inducing activity is an undesired side-effect.

The pharmacological activities of 9-oxo-11α,15α-dihydroxy-17S,20-dimethylprosta-trans-2,trans-13-dienoic acid, 9-oxo-11α,15α-dihydroxy-17R,20-dimethylprosta-trans-2,trans-13-dienoic acid and methyl 9-oxo-11α,15α-dihydroxy-17S,20-dimethylprosta-trans-2,trans-13-dienoate (compounds F, G and H in the following Table) and of prostaglandin analogues already disclosed in our British Pat. Nos. 1416410 and 1540427 for example 9-oxo11α,15α-dihydroxy-16R-methylprosta-trans-2,-trans-13-dienoic acid, 9-oxo-11α,15α-dihydroxy-17-ethylprosta-trans-13-dienoic acid, 9-oxo-11α,15α-dihydroxy-16-phenyl-18,19,20-trinorprosta-trans-2,trans-13-dienoic acid, 9-oxo-11α,15α-dihydroxy-17,20-diethylprosta-trans-2,trans-13-dienoic acid and methyl 9-oxo-11α,15α-dihydroxy-17,20-diethylprosta-trans-2,trans-13-dienoate are compared in the following Table. In the Table, all the activities are indicated relative to the activity of $PGE_1$, taken as 1.

TABLE

| Compound | Hypotensive Activity | | Inhibitory Activity on Blood Platelet Aggregation | | Vasodilator Activity | Diarrhoea-inducing Activity |
|---|---|---|---|---|---|---|
| | Dog (i.v.) | Rat (p.o.) | Rat | Human | Rabbit | Mice (p.o.) |
| A | 9.5 | | 2.84 | 1.6 | 2–3 | 270.6 |
| B | 1.5 | 10 | 14.5 | 22.1 | 1.0 | <1 |
| C | 39.0 | | | | 0.3 | 11.9 |
| D | 1.45 | 30–100 | 1.4 | 2.4 | <0.1 | 3.2 |
| E | 0.88 | 10 | 2.2 | 0.14 | 0.1 | 1.7 |
| F | 10.0 | 100 | 81.6 | 38.5 | 19.0 | <1 |
| G | 3.5 | | 70.5 | 48.1 | 14.0 | <1 |
| H | 5.0 | 100 | | | | <1 |

A: 9-oxo-11α,15α-dihydroxy-16R-methylprosta-trans-2,trans-13-dienoic acid.

B: 9-oxo-11α,15α-dihydroxy-17-ethylprosta-trans-2,trans-13-dienoic acid

C: 9-oxo-11α,15α-dihydroxy-16-phenyl-18,19,20-trinorprosta-trans-2,trans-13-dienoic acid D: 9-oxo-11α,15α-dihydroxy-17,20-diethylprosta-trans-2,trans-13-dienoic acid E: methyl 9-oxo-11α,15α-dihydroxy-17,20-diethylprosta-trans-2,trans-13-dienoate F: 9-oxo-11α,15α-dihydroxy-17S,20-dimethylprosta-trans-2,trans-13-dienoic acid G: 9-oxo-11a,15a-dihydroxy-171 R,20-dimethylprosta-trans-2,trans-13-dienoic acid H: methyl 9-oxo-11α,15α-dihydroxy-17S,20-dimethylprosta-trans-2,trans-13-dienoate As is to be noted from the Table, the compounds of the present invention (compounds F, G and H) possess extremely strong pharmacological useful activities in conjunction with a weaker diarrhoea-inducing (side-effect) activity when compared with the known compounds.

The very wide separation between the doses required to prouce desired and undesired pharmacological effects makes them especially suitable for the treatment, by oral administration, of the aforesaid disorders of the cardiovascular system. It will be noted that the compounds are even more active than the known compound 9-oxo-11α,15α-dihydroxy-17,20-diethylprosta-trans-2,trans-13-dienoic acid and its methyl ester (described in British Pat. No. 1,540,427, compounds which are particularly preferred for their hypotensive activity) in their useful activities and, in addition, possess a lower diarrhoea-producing activity.

Acute toxicity tests on the compounds of the present invention were conducted by administering them intravenously or orally to mice. For example, the $LD_{50}$ of 9-oxo-11α,15α-dihydroxy-17S,20-dimethylprosta-trans-2,trans-13-dienoic acid is about 12 mg/kg animal body weight by intravenous administration and about 50 mg/kg animal body weight by oral administration.

According to a feature of the present invention, trans-Δ²-prostaglandin analogues of general formula VI are prepared by the process which comprises hydrolysing the groups OR⁴ of compounds of the general formula:

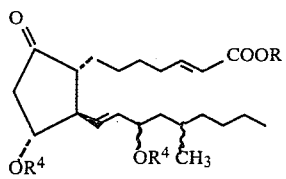
VII (wherein $R^4$ represents a tetrahydropyran-2-yl or tetrahydrofuran-2-yl group, each such group being unsubstituted or substituted by at least one alkyl group, or a 1-ethoxyethyl group, R and ~~~ are as hereinbefore defined and the depicted double bonds are trans) to hydroxy groups. $R^4$ preferably represents the tetrahydropyran-2-yl group.

The hydrolysis of the compounds of general formula VII may be carried out with (1) an aqueous solution of an organic acid, e.g. acetic acid, propionic acid, oxalic acid or p-toluenesulphonic acid, or an aqueous solution of an inorganic acid, e.g. hydrochloric acid, sulphuric acid or phosphoric acid, advantageously in the presence of an inert organic solvent miscible with water [for example, a lower alkanol such as methanol or ethanol (preferably methanol), or an ether such as 1,2-dimethoxyethane, dioxan or tetrahydrofuran (preferably tetrahydrofuran)], at a temperature from ambient to 75° C. (preferably at a temperature from ambient to 45° C.), (2) an anhydrous solution of an organic acid, e.g. p-toluenesulphonic acid or trifluoroacetic acid, in an anhydrous lower alkanol, e.g. methanol or ethanol, at a temperature from 10° to 45° C., or (3) an anhydrous solution of p-toluenesulphonic acid-pyridine complex in a lower alkanol, e.g. methanol or ethanol at a temperature from 10° to 60° C. Advantageously the mild hydrolysis under acidic conditions is carried out with a mixture of dilute hydrochloric acid and tetrahydrofuran, a mixture of dilute hydrochloric acid and methanol, a mixture of acetic acid, water and tetrahydrofuran, a mixture of phosphoric acid, water and tetrahydrofuran, or a mixture of p-toluenesulphonic acid-pyridine complex and anhydrous methanol.

The compounds of general formula VII may be prepared by oxidising to an oxo group the 9-hydroxy group of a compound of the general formula:

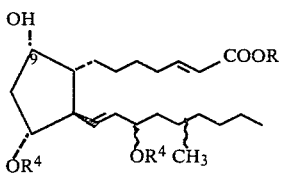
VIII (wherein the various symbols are as hereinbefore defined). This oxidation may be carried out by methods known per se for the conversion of a hydroxy group in the 9-position of a prostaglandin to an oxo group, for example by means of chromic acid solution (prepared from chromium trioxide, manganese sulphate, sulphuric acid and water) or Jones' reagent. By the term "methods known per se" as used in this specification is meant methods heretofore used or described in the chemical literature.

In formula VIII and in subsequent formulae in the specification carbon-carbon double bonds depicted

or are trans, and the wavy line ~ indicates attachment in α- or β-configuration or a mixture thereof.

The compounds of general formula VIII may be prepared by reacting a compound of the general formula:

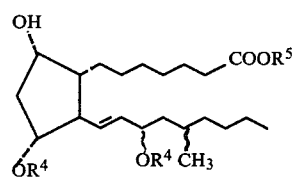
IX (wherein $R^5$ represents a straight- or branched-chain alkyl group containing from 1 to 4 carbon atoms, and the other symbols are as hereinbefore defined) with a lithium compound of the general formula:

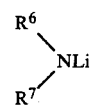
X (wherein $R^6$ and $R^7$, which may be the same or different, each represents a straight- or branched-chain alkyl group containing from 1 to 6 carbon atoms or a cycloalkyl group containing from 3 to 6 carbon atoms), e.g. lithium diisopropylamide, to obtain a lithium compound of the general formula:

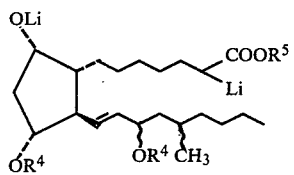
XI (wherein the various symbols are as hereinbefore defined), reacting the lithium compound with benzeneselenenyl bromide (i.e. φSeBr wherein φ represents the phenyl radical), diphenyl diselenide, or a dialkyl disulphide or diphenyl disulphide of the general formula $R^8SSR^8$ (wherein the symbols $R^8$ both represent an alkyl group containing from 1 to 4 carbon atoms or a phenyl group) and hydrolysing the resulting intermediate to convert the group —OLi attached to the cyclopentane ring to an α-hydroxy group and to obtain a compound of the general formula:

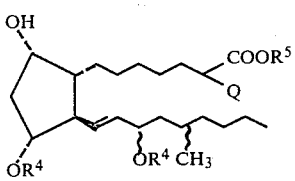

XII

[wherein Q represents —Seφ (wherein φ is as hereinbefore defined) or —SR⁸ (wherein R⁸ is as hereinbefore defined), and the other symbols are as hereinbefore defined], treating the resulting compound with hydrogen peroxide or sodium periodate and decomposing the resulting compound of the general formula:

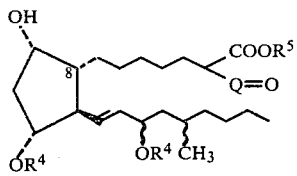

XIII (wherein the various symbols are as hereinbefore defined), to convert the grouping

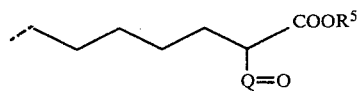

attached to the 8-position of the cyclopentane ring to a trans-$\Delta^2$-grouping

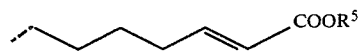

(wherein $R^5$ is as hereinbefore defined) i.e. to obtain a compound of the general formula:

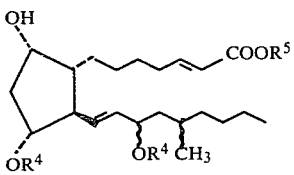

VIIIA (wherein the various symbols are as hereinbefore defined), and, if desired, hydrolysing the group —COOR⁵ of the compound of general formula VIIIA to a carboxy group to obtain the corresponding acid of the general formula:

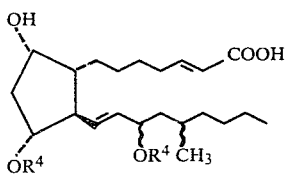

VIIIB wherein the various symbols are as hereinbefore defined.

The reaction between the prostaglandin compound of general formula IX and the lithium compound of general formula X is carried out in an organic solvent, for example by adding dropwise a solution of a prostaglandin compound of general formula IX in tetrahydrofuran to a solution of an amine of general formula X in tetrahydrofuran at a low temperature, e.g. −70° C., the ratio of the molecular equivalents of the compounds of general formula IX to X in the reaction mixture being 1:2 to 1:3. After the dropwise addition of the prostaglandin solution, the reaction mixture is stirred at the same temperature for about 30 minutes to obtain a solution of the lithium compound of general formula XI.

The reaction between the lithium compound of general formula XI and benzeneselenenyl bromide, diphenyl diselenide, dialkyl disulphide or diphenyl disulphide is preferably carried out in tetrahydrofuran, diethyl ether, n-hexane, n-pentane or a mixture of two or more of them (more preferably in tetrahydrofuran) at a low temperature, e.g. −70° C. Thus, to the lithium compound solution obtained as described above there is added a solution in tetrahydrofuran of 3 to 4 molecular equivalents of benzeneselenenyl bromide or diphenyl diselenide, or 2 to 3 molecular equivalents of dialkyl disulphide or diphenyl disulphide, for each molecular equivalent of lithium compound present, the temperature of the two solutions being −70° C. The reaction mixture is stirred at −70° C. (a) for one hour when a selenium compound is the reactant or (b) for 30 minutes when a disulphide is the reactant, and subsequently at ambient temperature, e.g. 15° C. for 30 minutes. After addition of, for example, a small amount of a saturated aqueous ammonium chloride solution to the solution of the resulting prostaglandin intermediate to hydrolyse the group —OLi attached to the cyclopentane ring to an α-hydroxy group, the product of general formula XII is extracted with ethyl acetate.

When the product of general formula XII is a compound wherein Q is benzeneselenenyl, i.e. —Seφ, the ethyl acetate solution of the product is then treated with 5 to 7 molecular equivalents of hydrogen peroxide at a temperature below 30° C., or with 5 molecular equivalents of sodium periodate in the presence of a lower alkanol (preferably methanol) and water, at a temperature below 20° C., preferably for about 24 hours, to obtain a compound of general formula XIII wherein O=Q— is benzeneseleninyl, i.e. —Se(O)φ. The reaction mixture is then stirred for one hour at 25° to 30° C. to decompose the compound to a compound of general formula VIIIA which can be separated from the reaction mixture by methods known per se and purified by column chromatography.

When the product of general formula XII is a compound wherein Q is a group —SR⁸ (wherein R⁸ is as hereinbefore defined), the product is separated from the ethyl acetate solution by methods known per se and treated with hydrogen peroxide or sodium periodate in the same manner as hereinbefore described for a product of general formula XII wherein Q is benzeneselenenyl to obtain a compound of general formula XIII wherein Q is a group —SR⁸ (wherein R⁸ is as hereinbefore defined), which can be separated from the reaction mixture by methods known per se.

When the compound of general formula XIII is a compound wherein Q represents an alkylthio group —SR⁹ (wherein R⁹ represents an alkyl group containing from 1 to 4 carbon atoms), the compound is dissolved in toluene and the solution stirred, preferably in the presence of a small amount of calcium carbonate, at a temperature of 100° to 120° C. for a period ranging from 5 to 24 hours to decompose the compound to a compound of general formula VIIIA. When the compound of general formula XIII is a compound wherein Q represents the phenylthio group, the compound is dissolved in carbon tetrachloride and the solution stirred, preferably in the presence of a small amount of calcium carbonate, at a temperature of about 50° C. for a period ranging from 5 to 24 hours to decompose the compound to a compound of general formula VIIIA.

The hydrolysis of the alkyl ester of general formula VIIIA to the corresponding acid of general formula VIIIB is carried out by methods known per se. For example, it is carried out by treating the ester with an aqueous solution of a hydroxide or carbonate of an alkali metal (e.g. sodium or potassium) in the presence of an organic solvent miscible with water, for example tetrahydrofuran or an alkanol containing from 1 to 4 carbon atoms such as methanol.

The compounds of general formula X for example lithium diisopropylamide and benzeneselenenyl bromide and diphenyl diselenide used for the aforesaid reactions can be prepared by methods known per se, for example as described in J. Amer. Chem. Soc., 95, 6139 (1973).

The compounds of general formula IX may be prepared by the hydrolysis under alkaline conditions of a compound of the general formula:

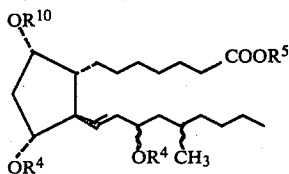

XIV wherein $R^{10}$ represents an alkanoyl group containing from 2 to 5 carbon atoms, and the other symbols are as hereinbefore defined. The hydrolysis under alkaline conditions may be effected with anhydrous potassium carbonate in an anhydrous alkanol containing from 1 to 4 carbon atoms, preferably absolute methanol.

The compounds of general formula XIV may be prepared by reacting a compound of the general formula:

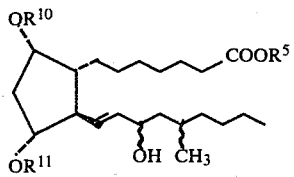

XV (wherein $R^{11}$ represents a hydrogen atom or a tetrahydropyran-2-yl or tetrahydrofuran-2-yl group, each such group being unsubstituted or substituted by at least one alkyl group, or a 1-ethoxyethyl group, and the other symbols are as hereinbefore defined) with a dihydropyran, a dihydrofuran or ethyl vinyl ether in an inert organic solvent, e.g. methylene chloride, in the presence of a condensing agent, e.g. p-toluenesulphonic acid.

The compounds of general formula XV wherein $R^{11}$ represents a hydrogen atom, i.e. the compounds of general formula:

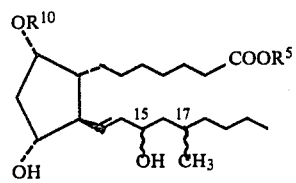

XVA (wherein the various symbols are as hereinbefore defined) may be prepared by hydrolysing a compound of the general formula:

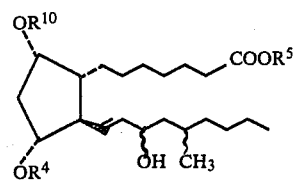

XVB (wherein the various symbols are as hereinbefore defined) in the same manner as hereinbefore described for the hydrolysis of the compounds of general formula VII.

Four isomers of the compound of general formula XVA based on the asymmetric carbon atoms in 15- and 17-positions are possible. If necessary, these four isomers can be separated from each other by methods known per se, e.g. thin layer, column or high-speed liquid chromatography on silica gel.

The compounds of general formula XVB may be prepared by reducing the 15-oxo group of a compound of the general formula:

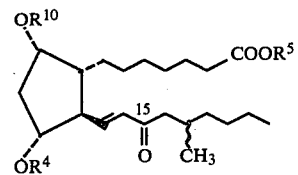

XVI (wherein the various symbols are as hereinbefore defined) to a hydroxy group. The reduction is suitably carried out with excess sodium borohydride in an alkanol containing from 1 to 4 carbon atoms, e.g. methanol at a low temperature (preferably at $-60°$ to $-30°$ C.), or with zinc borohydride in a suitable inert organic solvent such as 1,2-dimethoxyethane at a temperature of $-10°$ to $10°$ C. The product thus obtained is a mixture of isomers in which the 15-hydroxy group is in $\alpha$- or $\beta$-configuration. If desired the isomer having the hydroxy group in $\alpha$-configuration may be separated from the isomer having the hydroxy group in $\beta$-configuration by column chromatography on silica gel.

The compounds of general formula XVI may be prepared by the Wittig reaction of a compound of the general formula:

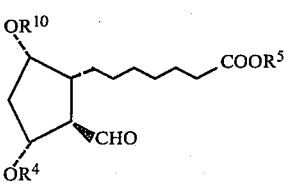

XVII (wherein the various symbols are as hereinbefore defined) with the sodio derivative of a dialkyl phosphonate of the general formula:

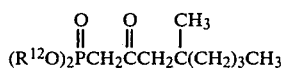

$$(R^{12}O)_2 \overset{O}{\overset{\|}{P}} CH_2 \overset{O}{\overset{\|}{C}} CH_2 \overset{CH_3}{\overset{|}{C}} (CH_2)_3 CH_3 \quad \text{XVIII}$$

wherein $R^{12}$ represents an alkyl group containing from 1 to 4 carbon atoms. The reaction is preferably effected by suspending sodium hydride in an inert organic solvent e.g. tetrahyrofuran or 1,2-dimethoxyethane, and adding the dialkyl phosphonate of general formula XVIII. The resulting sodio derivative of the dialkyl phosphonate may then be reacted with the compound of general formula XVII at a temperature of 20° to 45° C. for 1 to 5 hours to form the trans-enone compound of general formula XVI stereoselectively.

The compounds of general formula XVII are known compounds and can be prepared as described in, for example, British Pat. No. 1,545,213.

The dialkylphosphonates of general formula XVIII may be prepared by reacting a solution of n-butyllithium in an inert organic solvent e.g. diethyl ether or hexane, with a solution of a dialkyl methylphosphonate of the general formula:

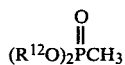

$$(R^{12}O)_2 \overset{O}{\overset{\|}{P}} CH_3 \quad \text{XIX}$$

(wherein $R^{12}$ is as hereinbefore defined), e.g. dimethyl methylphosphonate or diethyl methylphosphonate at a temperature below $-50°$ C., and then adding dropwise to the reaction mixture a solution of sec-butyl 3-methylheptanoate in tetrahydrofuran at a temperature below $-50°$ C., stirring the reaction mixture below $-50°$ C., and then stirring at a suitable low temperature e.g. from 0° C. to ambient temperature.

The sec-butyl 3-methylheptanoate may be prepared by reacting sec-butyl crotonate with n-butyl-magnesium bromide in the presence of cuprous chloride, and hydrolysing the resulting reaction product by, for example, treating with an acid such as hydrochloric acid.

If desired, the compounds of general formula VI wherein R represents a hydrogen atom can be converted by methods known per se into non-toxic salts.

By the term "non-toxic salts", as used in this specification, is meant salts the cations of which are relatively innocuous to the animal organism when used in therapeutic doses so that the beneficial pharmacological properties of the compounds of general formula VI are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing 2 or 3 carbon atoms.

The non-toxic salts may be prepared from the acids of general formula VI wherein R represents a hydrogen atom by, for example, reaction of stoichiometric quantities of an acid of general formula VI and the appropriate base, e.g. an alkali metal hydroxide or carbonate, ammonium hydroxide, ammonia or an amine, in a suitable solvent. The salts may be isolated by lyophilisation of the solution, or, if sufficiently insoluble in the reaction medium, by filtration, if necessary after removal of part of the solvent.

The prostaglandin analogues of general formula VI may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated or by cooling and separating the product by filtration or decantation. The ratio of organic solvent to water may be varied according to the solubilities of the starting materials and products. Preferably the temperature is not allowed to exceed 70° C., during the preparation of the cyclodextrin clathrates. $\alpha$, $\beta$- or $\gamma$-Cyclodextrins or mixtures thereof may be used in the preparation of the cyclodextrin clathrates. The conversion into their cyclodextrin clathrates serves to increase the stability of the prostaglandin compounds.

The following Reference Examples and Examples illustrate the present invention. In them "TLC", "IR" and "NMR" represent "Thin layer chromatography", "Infrared absorption spectrum" and "Nuclear magnetic resonance spectrum" respectively. Where solvent ratios are specified in chromatographic separations, the ratios are by volume: the developing solvents used are shown in parenthesis.

REFERENCE EXAMPLE 1 sec-Butyl 3-methylheptanoate

Several drops of a solution of 4.9 g of n-butyl bromide in 126 ml of dry diethyl ether were added to a suspension of 10.53 g of magnesium and a trace amount of iodine in 80 ml of dry diethyl ether, and the mixture was stirred vigorously. The colour of the iodine disappeared upon slight heating, and the rest of the n-butyl bromide solution was then added dropwise at a rate sufficient to maintain a constant reflux of the reaction mixture. After addition of the n-butyl bromide solution the reaction mixture was heated to reflux for a further 15 minutes and was then cooled to 5° C. with an ice-water bath. Cuprous chloride (0.589 g) was divided into seven equal portions: one portion was added to the reaction mixture and then a solution of 23.9 g of sec-butyl crotonate in 120 ml of dry diethyl ether was added dropwise over 3 hours, during which time the six remaining portions of cuprous chloride were added at 30-minute intervals. After stirring the mixture at 5° C. for 15 minutes and then at room temperature for 1 hour, the reaction mixture was gradually poured into an ice-cooled mixture of 150 g of ice, 50 ml of concentrated hydrochloric acid and 60 ml of diethyl ether with vigorous stirring. The organic layer was separated from the reaction mixture obtained and the aqueous layer was extracted with diethyl ether. The organic layer was washed with a saturated aqueous solution of sodium bicarbonate and a saturated aqueous solution of sodium chloride, dried over magnesium sulphate, and then concentrated. The residue was purified by distillation under reduced pressure to give 27.8 g of the title compound having the following physical characteristics:

boiling point: 109°–111° C./28 mmHg;
NMR (CDCl$_3$ solution): δ=4.85 (1H, m), 2.46–2.05 (2H, d),
2.05–1.75 (1H, m), 1.20 (3H, d), 1.08–0.70 (9H, t).

REFERENCE EXAMPLE 2

Dimethyl 2-oxo-4-methyloctylphosphonate

Under an atmosphere of nitrogen, 375 ml of a 1.33 M solution of n-butyllithium in n-hexane were added dropwise to a solution of 61.9 g of dimethyl methylphosphonate in 587 ml of tetrahydrofuran at −70° C. After stirring the mixture for one hour at −70° C., a solution of 40 g of sec-butyl 3-methylheptanoate (prepared as described in Reference Example 1) in 70 ml of tetrahydrofuran was added dropwise at −70° C., and the mixture was stirred at the same temperature for 4 hours and then stirred overnight at room temperature. The reaction mixture was then acidified with acetic acid and filtered to remove the precipitated solid, and the filtrate was concentrated under reduced pressure. The residue was diluted with ethyl acetate, washed with water and a saturated aqueous solution of sodium chloride, dried over magnesium sulphate and concentrated under reduced pressure. The residue was purified by distillation under reduced pressure to give 42 g of the title compound having the following physical characteristics:
boiling point: 115°–120° C./0.09 mmHg;
NMR (CDCl$_3$ solution): δ=3.78 (6H, d), 3.08 (2H, d), 2.75–2.23 (2H, m), 2.20–1.30 (1H, m), 1.05–0.71 (6H, td).

REFERENCE EXAMPLE 3

Methyl 9α-acetoxy-11α-(tetrahydropyran-2-yloxy)-15-oxo-17RS,20-dimethylprost-trans-13-enoate Under an atmosphere of nitrogen, a solution of 9.33 g of dimethyl 2-oxo-4-methyloctylphosphonate (prepared as described in Reference Example 2) in 20 ml of tetrahydrofuran was added dropwise to a suspension of 597 mg of sodium hydride in 130 ml of tetrahydrofuran at room temperature with stirring and the mixture was stirred until the solution became clear. To the solution thus obtained was added a solution of 6.613 g of 1α-acetoxy-2α-(6-methoxycarbonylhexyl)-3β-formyl-4α-(tetrahydropyran-2-yloxy)cyclopentane (described in Reference Example 21 of British Pat. No. 1,545,213) in 20 ml of tetrahydrofuran and the mixture was stirred at room temperature for 30 minutes. The reaction mixture was then acidified with acetic acid and filtered through a pad of magnesium sulphate, and the filtrate was concentrated under reduced pressure. The residue was diluted with 300 ml of ethyl acetate, washed with a saturated aqueous solution of sodium bicarbonate, water and a saturated aqueous solution of sodium chloride, dried over magnesium sulphate, and concentrated under reduced pressure. The residue was purified by column chromatography on silica gel using a mixture of benzene and ethyl acetate (4:1) as eluent to give 7.511 g of the title compound having the following physical characteristic:
NMR (CDCl$_3$ solution): δ=7.1–5.9 (2H, m), 5.3–4.8 (1H, m), 4.6–4.3 (1H, m).

REFERENCE EXAMPLE 4

Methyl 9α-acetoxy-11α,15α-dihydroxy-17S,20-dimethylprost-trans-13-enoate and methyl 9α-acetoxy-11α,15α-dihydroxy-17R,20-dimethylprost-trans-13-enoate To a solution of 7.511 g of methyl 9α-acetoxy-11α(-tetrahydropyran-2-yloxy)-15-oxo-17RS,20-dimethyl-prost-trans-13-enoate (prepared as described in Reference Example 3) in 75 ml of methanol was added portionwise 1.0 g of sodium borohydride at −50° C. After 30 minutes of stirring at −50° C. to −40° C., the reaction mixture was acidified with acetic acid and concentrated under reduced pressure. The residue was diluted with ethyl acetate, washed with a saturated aqueous solution of sodium bicarbonate and a saturated aqueous solution of sodium chloride, dried over magnesium sulphate and concentrated under reduced pressure to give methyl 9α-acetoxy-11α-(tetrahydropyran-2-yloxy)-15αβ-hydroxy-17RS,20-dimethylprost-trans-13-enoate (7.791 g as crude product).

To a solution of the crude product obtained in 100 ml of methanol was added 150 mg of p-toluenesulphonic acid and the mixture was stirred at 40° C. for 20 minutes. The solution was adjusted to pH 8 with an aqueous solution of sodium bicarbonate, and then the mixture was concentrated under reduced pressure. The residue was diluted with 300 ml of ethyl acetate, washed with water and a saturated aqueous solution of sodium chloride, dried over magnesium sulphate, and concentrated under reduced pressure. The residue was purified by column chromatography on silica gel using a mixture of benzene and ethyl acetate (1:1) as eluent to give 3.052 g of methyl 9α-acetoxy-11α,15α-dihydroxy-17RS,20-dimethylprost-trans-13-enoate and 2.727 g of methyl 9α-acetoxy-11α,15β-dihydroxy-17RS,20-dimethylprost-trans-13-enoate having the following physical characteristic:
TLC (developing solvent, benzene:ethyl acetate=1:2): Two spots at Rf=0.21 and 0.25, (15α-isomer) Two spots at Rf=0.42 and 0.46, (15β-isomer)

3 g of the 15α-isomer obtained was further purified by column chromatography on silica gel using a mixture of benzene and ethyl acetate (1:2) as eluent to give 1.056 g of methyl 9α-acetoxy-11α,15α-dihydroxy-17S,20-dimethylprost-trans-13-enoate and 1.273 g of methyl 9α-acetoxy-11α,15α-dihydroxy-17R,20-dimethylprost-trans-13-enoate having the following physical characteristics: 17S-isomer:
TLC (developing solvent, benzene:ethyl acetate=1:2): Rf=0.20;
NMR (CDCl$_3$ solution): δ=5.76–5.30 (2H, m), 5.30–4.92 (1H, m), 4.34–3.11 (5H, m), 3.00 (2H, bs), 1.02–0.71 (6H, m). 17R-isomer:
TLC (developing solvent, benzene:ethyl acetate=1:2): Rf=0.26;
NMR (CDCl$_3$ solution): δ=5.76–5.30 (2H, m), 5.30–4.92 (1H, m), 4.34–3.11 (5H, m), 2.82–2.31 (2H, bs), 1.02–0.71 (6H, m).

REFERENCE EXAMPLE 5

Methyl 9α-hydroxy-11α,15α-bis(tetrahydropyran-2-yloxy)17S,20-dimethylprost-trans-13-enoate A mixture of 1.05 g of methyl 9α-acetoxy-11α,15α-dihydroxy-17S,20-dimethylprost-trans-13-enoate (prepared as described in Reference Example 4), 0.744 ml of 2,3-dihydropyran, 5 mg of p-toluenesulphonic acid and 7 ml of methylene chloride was stirred at room temperature for 15 minutes, and several drops of pyridine were then added to the mixture to stop the reaction. The reaction mixture was diluted with 60 ml of ethyl acetate, washed with a saturated aqueous solution of sodium bicarbonate and a saturated aqueous solution of sodium chloride, dried over magnesium sulphate, and concentrated under reduced pressure to give methyl 9α-acetoxy-11α,15α-bis(tetrahydropyran-2-yloxy)-17S,20-dimethylprost-trans-13-enoate (2.33 g as crude product).

A mixture of the crude product obtained, 1.32 g of potassium carbonate and 35 ml of methanol was stirred at 40° C. for one hour, the reaction mixture was acidified with acetic acid at 0° C., diluted with 200 ml of ethyl acetate, washed with a saturated aqueous solution of sodium bicarbonate and a saturated aqueous solution of sodium chloride, dried over magnesium sulphate, and concentrated under reduced pressure. The residue was purified by column chromatography on silica gel using a mixture of benzene and ethyl acetate (4:1) as eluent to give 1.135 g of the title compound having the following physical characteristic:

TLC (developing solvent, benzene:ethyl acetate=3:1): Rf=0.47.

REFERENCE EXAMPLE 6

Methyl 2-phenylseleno-9α-hydroxy-11α,15α-bis(tetrahydropyran-2-yloxy)-17S,20-dimethylprost-trans-13-enoate Under an atmosphere of nitrogen, 3.29 ml of a 1.6 M solution of n-butyllithium in n-hexane were added dropwise to a solution of 0.738 ml of diisopropylamine in 20 ml of tetrahydrofuran at −70° C. and the mixture was stirred at the same temperature for 20 minutes to give the lithium diisopropylamide solution. To the solution obtained was added dropwise a solution of 1.135 g of methyl 9α-hydroxy-11α,15α-bis(tetrahydropyran-2-yloxy)-17S,20-dimethylprost-trans-13-enoate (prepared as described in Reference Example 5) in 6 ml of tetrahydrofuran at −70° C. and the mixture was stirred at that temperature for 20 minutes. To the solution thus obtained was added dropwise a solution of 1.31 g of diphenyldiselenide in 6 ml of tetrahydrofuran at −70° C. and the mixture was stirred at the same temperature for 45 minutes and then at 0° C. for one hour. The reaction mixture was then poured into 50 ml of a saturated aqueous solution of ammonium chloride and extracted with ethyl acetate. The extract was washed with water and a saturated aqueous solution of sodium chloride, dried over magnesium sulphate and concentrated under reduced pressure. The residue was purified by column chromatography on silica gel using a mixture of benzene and ethyl acetate (3:1) as eluent to give 1.131 g of the title compound having the following physical characteristic:

TLC (developing solvent, benzene:ethyl acetate=3:1): Rf=0.56.

REFERENCE EXAMPLE 7

Methyl 9α-hydroxy-11α,15α-bis(tetrahydropyran-2-yloxy)17S,20-dimethylprosta-trans-2,trans-13-dienoate 0.44 g of sodium bicarbonate was added to a solution of 1.13 g of methyl 2-phenylseleno-9α-hydroxy-11α,15α-bis(tetrahydropyran-2-yloxy)-17S,20-dimethylprost-trans-13-enoate (prepared as described in Reference Example 6) in a mixture of 10 ml of ethyl acetate and 5 ml of tetrahydrofuran, then 0.526 ml of a 30% (v/v) aqueous solution of hydrogen peroxide was added dropwise to the mixture at 35° C. The mixture was stirred at the same temperature for 30 minutes. The reaction mixture was then diluted with 50 ml of ethyl acetate, washed with a saturated aqueous solution of sodium bicarbonate and a saturated aqueous solution of sodium chloride, dried over magnesium sulphate and concentrated under reduced pressure to give 0.92 g of the title compound having the following physical characteristics:

TLC (developing solvent, benzene:ethyl acetate=3:1): Rf=0.48;

NMR (CDCl$_3$ solution): δ=6.98 (1H, dt), 5.81 (1H, dt), 5.69–5.20 (2H, m), 4.82–4.52 (2H, m), 4.30–3.20 (11H, m), 1.02–0.70 (6H, t).

REFERENCE EXAMPLE 8

Methyl 9α-hydroxy-11α,15α-bis(tetrahydropyran-2-yloxy)17R,20-dimethylprosta-trans-2,trans-13-dienoate By proceeding as described in Reference Examples 5, 6 and 7 but using 1.27 g of methyl 9α-acetoxy-11α,15α-dihydroxy-17R,20-dimethylprost-trans-13-enoate (prepared as described in Reference Example 4) instead of methyl 9α-acetoxy-11α,15α-dihydroxy-17S,20-dimethylprost-trans-13-enoate used as starting material in Reference Example 5, there were obtained 1.1 g of the title compound having the following physical characteristics:

TLC (developing solvent, benzene:ethyl acetate=2:1): Rf=0.44;

NMR (CDCl$_3$ solution): δ=6.96 (1H, dt), 5.80 (1H, d), 5.68–5.15 (2H, m), 4.85–4.55 (2H, m), 4.39–3.25 (7H, m), 3.71 (3H, s).

REFERENCE EXAMPLE 9

9α-Hydroxy-11α,15α-bis(tetrahydropyran-2-yloxy)-17S, 20-dimethylprosta-trans-2,trans-13-dienoic acid To a solution of 0.9 g of methyl 9α-hydroxy-11α,15α-bis(tetrahydropyran-2-yloxy)-17S,20-dimethylprosta-trans-2,trans-13-dienoate (prepared as described in Reference Example 7) in 20 ml of ethanol was added 20 ml of a 2 N aqueous solution of potassium hydroxide, the mixture was stirred at room temperature for 1.5 hours, then acidified with 1 N hydrochloric acid at 0° C. and extracted with ethyl acetate. The organic layer was washed with water and a saturated aqueous solution of sodium chloride, dried over magnesium sulphate and concentrated under reduced pressure to give 0.705 g of the title compound having the following physical characteristic:

TLC (developing solvent, methylene chloride:methanol=20:1): Rf=0.26.

EXAMPLE 1

9-Oxo-11α,15α-dihydroxy-17S,20-dimethylprosta-trans-2,trans-13-dienoic acid (17S,20-dimethyl-trans-2,3-didehydro-PGE$_1$)

To a solution of 0.7 g of 9α-hydroxy-11α,15α-bis(tetrahydropyran-2-yloxy)-17S,20-dimethylprosta-trans-2,trans-13-dienoic acid (prepared as described in Reference Example 9) in 30 ml of diethyl ether was added 44 ml of a chromic acid solution (prepared by adding 5.05 ml of sulphuric acid and 4.58 g of chromium trioxide to an aqueous solution of 16 g of manganese sulphate in 114 ml of water) at 0° C. and the mixture was stirred for 2 hours at the same temperature. The reaction mixture was extracted with diethyl ether. The extract was washed with water and a saturated aqueous solution of sodium chloride, dried over magnesium sulphate and concentrated under reduced pressure to give 9-oxo-11α,15α-bis(tetrahydropyran-2-yloxy)17S,20-dimethyl-prosta-trans-2,trans-13-dienoic acid (0.724 g as a crude product).

The crude product obtained was dissolved in a mixture of 3 ml of tetrahydrofuran and 30 ml of 65% (v/v) aqueous acetic acid and the mixture was stirred at 40° C. for 1.5 hours. The reaction mixture was then poured into 150 ml of ice-water, and extracted with ethyl acetate. The extract was washed with water and a saturated aqueous solution of sodium chloride, dried over magnesium sulphate and concentrated under reduced pressure. The residue was purified by column chromatography on silica gel using a mixture of cyclohexane and ethyl acetate (1:2) as eluent to give 254 mg of the title compound (as white crystals) having the following physical characteristics: melting point: 97°–100° C.;

TLC (developing solvent, chloroform:tetrahydrofuran:acetic acid = 10:2:1): Rf = 0.26;

NMR (CDCl$_3$ solution): $\delta$ = 7.20–6.78 (1H, dt), 6.30–5.32 (6H, m), 4.40–3.74 (2H, m), 2.25 (1H, dd), 1.05–0.55 (6H, m).

EXAMPLE 2

Methyl 9-oxo-11α,15α-dihydroxy-17S,20-dimethylprostatrans-2,trans-13-dienoate
(17S,20-dimethyl-trans-2,3-didehydro-PGE$_1$ methyl ester)

By proceeding as described in Example 1, 19 mg of the title compound, having the following physical characteristics, were obtained from 70 mg of methyl 9α-hydroxy-11α,15α-bis(tetrahydropyran-2-yloxy)-17S,20-dimethylprosta-trans-2,trans-13-dienoate (prepared as described in Reference Example 7).

TLC (developing solvent, chloroform:tetrahydrofuran:acetic acid = 20:2:1): Rf = 0.20;

IR (liquid film): $\nu$ = 3400, 1750, 1730, 1660, 980 cm$^{-1}$.

EXAMPLE 3

9-Oxo-11α,15α-dihydroxy-17R, 20-dimethylprosta-trans-2,trans-13-dienoic acid
(17R,20-dimethyl-trans-2,3-didehydro-PGE$_1$)

By proceeding as described in Reference Example 9 and Example 1 but using 1.1 g of methyl 9α-hydroxy-11α,15α-bis(tetrahydropyran-2-yloxy)-17R,20-dimethylprosta-trans-2,trans-13-dienoate (prepared as described in Reference Example 8) instead of methyl 9α-hydroxy-11α,15α-bis(tetrahydropyran-2-yloxy)-17S,20-dimethylprosta-trans-2,trans-13-dienoate used as starting material in Reference Example 9, there were obtained 161 mg of the title compound having the following physical characteristics:

TLC (developing solvent, chloroform:tetrahydrofuran:acetic acid = 10:2:1): Rf = 0.23;

NMR (CDCl$_3$ solution): $\delta$ = 7.02 (1H, dt), 5.80 (1H, d), 5.7–5.4 (2H, m), 4.4–3.8 (2H, m); IR (liquid film): $\nu$ = 3400, 2940, 2870, 1740, 1700, 1600, 1380, 1250, 980 cm$^{-1}$.

The present invention includes within its scope pharmaceutical compositions which comprise at least one new therapeutically useful compound of general formula VI or a cyclodextrin clathrate thereof or, when R represents a hydrogen atom, a non-toxic salt thereof, together with a pharmaceutical carrier or coating. In clinical practice the new compounds of the present invention will normally be administered orally, rectally or parenterally.

Solid compositions for oral administration include compressed tablets, pills, dispersible powders, and granules. In such solid compositions one or more of the active compounds is, or are, admixed with at least one inert diluent such as calcium carbonate potato starch, alginic acid, mannitol or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. The compositions may also include adjuvants such as preversing, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained,. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the human adult, the doses per person are generally between 0.5 µg and 200 µg, preferably 1 µg and 50 µg, by oral administration as vasodilator and antihypertensive agents, in the treatment of cardiac angina, and in the treatment and prevention of myocardial infarction, thrombosis and arteriosclerosis. The dose employed depends upon the route of administration, the duration of the treatment and the age, weight and condition of the patient.

The following Example illustrate pharmaceutical compositions according to the invention.

EXAMPLE 4

Dry mannitol was added to a mixture of 20 mg of 17S,20-dimethyl-trans-2,3-didehydro-PGE$_1$, 2 g of carboxymethyl cellulose calcium, 0.2 g of silicon dioxide and 2 g of magnesium stearate to give a total of 100 g of mixture. The mixture was well mixed to make it uniform, and then subjected to direct compression tabletting in a conventional manner using punches to give 1,000 tablets each containing 20 μg of the active material.

We claim:

1. A prostaglandin analogue of the general formula:

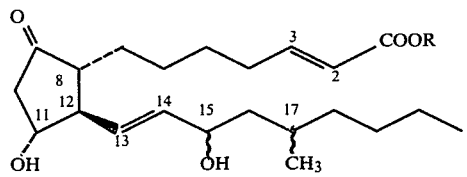

VI (wherein R represents a hydrogen atom or a straight- or branched-chain alkyl group containing from 1 to 4 carbon atoms, the wavy line ⁓ indicates attachment of α- or β-configuration or a mixture thereof, and the double bonds between $C_2$–$C_3$ and $C_{13}$–$C_{14}$ are trans), and cyclodextrin clathrates of such acids and esters, and when R represents a hydrogen atom, non-toxic salts of such acids.

2. Prostaglandin compounds according to claim 1 wherein the hydroxy group attached to the 15-position carbon atom is in α-configuration.

3. A prostaglandin analogue according to claim 1 which is 9-oxo-11α,15α-dihydroxy-17S,20-dimethylprosta-trans-2,trans-13-dienoic acid and cyclodextrin clathrates and non-toxic salts of the acid.

4. A prostaglandin analogue according to claim 1 which is methyl 9-oxo-11α,15α-dihydroxy-17S,20-dimethylprosta-trans-2,trans-13-dienoate and cyclodextrin clathrates thereof.

5. A prostaglandin analogue according to claim 1 which is 9-oxo-11α,15α-dihydroxy-17R,20-dimethylprosta-trans-2,trans-13-dienoic acid and cyclodextrin clathrates and non-toxic salts of the acid.

6. A prostaglandin analogue according to claim 1 which is methyl 9-oxo-11α,15α-dihyroxy-17R,20-dimethylprosta-trans-2,trans-13-dienoate and cyclohextrin clathrates thereof.

7. A compound of general formula VII

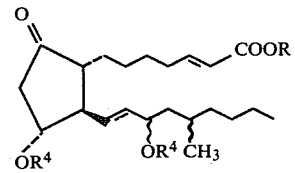

VII wherein R$^4$ represents a tetrahydropyran-2-yl or tetrahydrofuran-2-yl group, each such group being unsubstituted or substituted by at least one alkyl group, or a 1-ethoxyethyl group; the wavy line ⁓ indicates attachment in α- or β-configuration or a mixture thereof; R represents a hydrogen atom or a straight or branched chain alkyl group containing from 1 to 4 carbon atoms; the double bonds between $C_2$–$C_3$ and $C_{13}$–$C_{14}$ are trans.

8. A pharmaceutical composition which comprises, as active ingredient, at least one prostaglandin analogue as claimed in claim 1, or a cyclodextrin clathrate of such a prostaglandin analogue or, when R in the general formula depicted in claim 1 represents a hydrogen atom, a non-toxic salt of such a prostaglandin analogue, in association with a pharmaceutical carrier or coating.

9. A pharmaceutical composition according to claim 8 in which the active ingredient is a prostaglandin compound as claimed in claim 3, 4, 5 or 6.

10. A method for the treatment of cardiac angina and the prevention and treatment of myocardial infarction, thrombosis and arteriosclerosis in the human adult which comprises the administration of an effective amount of a prostaglandin analogue as claimed in claim 1 or a cyclodextrin clathrate thereof or, when R in formula VI depicted in claim 1 represents a hydrogen atom, a non-toxic salt thereof.

11. A method according to claim 10 in which the prostaglandin compound is administered orally and the amount is between 1 μg and 50 μg.

* * * * *

UNITED STATES PATENT AND TRADEMARK OFFICE
CERTIFICATE OF CORRECTION

PATENT NO. : 4,294,849
DATED : October 13, 1981
INVENTOR(S) : Masaki Hayashi et al It is certified that error appears in the above-identified patent and that said Letters Patent is hereby corrected as shown below:

On the title page assignee should read

-- (73) Assignee: Ono Pharmaceutical Co., Ltd., Osaka, Japan --.

*Signed and Sealed this*

*Twenty-seventh* Day of *March 1984*

[SEAL]

*Attest:*

GERALD J. MOSSINGHOFF

*Attesting Officer*     *Commissioner of Patents and Trademarks*